United States Patent
Zito, Jr.

(10) Patent No.: US 9,443,369 B2
(45) Date of Patent: *Sep. 13, 2016

(54) USER-SPECIFIC DISPENSING SYSTEM

(76) Inventor: Arthur J. Zito, Jr., Millersville, MD (US)

( * ) Notice: Subject to any disclaimer, the term of this patent is extended or adjusted under 35 U.S.C. 154(b) by 1162 days.

This patent is subject to a terminal disclaimer.

(21) Appl. No.: 11/280,157

(22) Filed: Nov. 16, 2005

(65) Prior Publication Data

US 2006/0106489 A1    May 18, 2006

Related U.S. Application Data

(63) Continuation-in-part of application No. 10/990,595, filed on Nov. 17, 2004.

(51) Int. Cl.
| | | |
|---|---|---|
| *G06F 17/00* | (2006.01) | |
| *G07F 9/00* | (2006.01) | |
| *G07F 17/32* | (2006.01) | |
| *A63F 13/40* | (2014.01) | |

(52) U.S. Cl.
CPC ............. *G07F 9/00* (2013.01); *A63F 13/10* (2013.01); *G07F 17/32* (2013.01)

(58) Field of Classification Search
CPC ........................................................ G07F 9/00
USPC .................................. 700/231–244; 463/23
See application file for complete search history.

(56) References Cited

U.S. PATENT DOCUMENTS

| | | | |
|---|---|---|---|
| 4,915,205 A | 4/1990 | Reid et al. | |
| 4,982,346 A | 1/1991 | Girouard et al. | |
| 5,072,380 A | 12/1991 | Randelman et al. | |
| 5,231,568 A | 7/1993 | Cohen et al. | |
| 5,267,171 A | 11/1993 | Suzuki et al. | |
| 5,373,440 A | 12/1994 | Cohen et al. | |
| 5,482,139 A | 1/1996 | Rivalto | |
| 5,642,485 A | 6/1997 | Deaton et al. | |
| 5,697,951 A | 12/1997 | Harpstead et al. | |
| 5,735,742 A | 4/1998 | French | |

(Continued)

FOREIGN PATENT DOCUMENTS

| | | | |
|---|---|---|---|
| EP | 1 426 905 A | 6/2004 | |
| JP | 03006692 A | 1/1991 | |

(Continued)

OTHER PUBLICATIONS

MedVantx Product Overview (received from MedVantx, Inc. Apr. 7, 2005).

(Continued)

*Primary Examiner* — Michael K Collins
(74) *Attorney, Agent, or Firm* — GTC Law Group PC & Affiliates

(57) ABSTRACT

The invention provides a system to physically dispense an item, including tangible items and/or services or features, on-site from a dispenser whereby the item to be dispensed is selected by the system based on user-specific or item-specific information. In an embodiment, the system selects the dispensed item based on both user-specific and item-specific information. In another embodiment the invention comprises a system that activates gaming features in a gaming device based on user-specific information. In another embodiment, the invention comprises a system incorporated into an interactive amusement system to activate features of a playfield based on user-specific information.

48 Claims, 7 Drawing Sheets

(56) References Cited

U.S. PATENT DOCUMENTS

| | | | |
|---|---|---|---|
| 5,857,175 A | 1/1999 | Day et al. | |
| 6,021,362 A * | 2/2000 | Maggard et al. | 700/234 |
| 6,100,881 A | 8/2000 | Gibbons et al. | |
| 6,110,041 A | 8/2000 | Walker et al. | |
| 6,110,155 A | 8/2000 | Baudino | |
| 6,182,857 B1 | 2/2001 | Hamm et al. | |
| 6,234,896 B1 | 5/2001 | Walker et al. | |
| 6,348,042 B1 | 2/2002 | Warren, Jr. | |
| 6,352,478 B1 | 3/2002 | Gabai et al. | |
| 6,412,654 B1 | 7/2002 | Cleeve | |
| 6,520,544 B1 | 2/2003 | Mitchell et al. | |
| 6,578,735 B1 * | 6/2003 | Mothwurf | 221/255 |
| 6,645,068 B1 | 11/2003 | Kelly et al. | |
| 6,658,323 B2 | 12/2003 | Tedesco et al. | |
| 6,837,427 B2 | 1/2005 | Overhultz et al. | |
| 6,854,642 B2 | 2/2005 | Metcalf et al. | |
| 6,874,612 B1 | 4/2005 | Uland | |
| 6,967,566 B2 * | 11/2005 | Weston et al. | 340/323 R |
| 7,172,197 B2 | 2/2007 | Wilson et al. | |
| 7,326,118 B2 | 2/2008 | Shinoda | |
| 7,383,509 B2 | 6/2008 | Foote et al. | |
| 7,398,921 B2 * | 7/2008 | Zito, Jr. | 235/381 |
| 7,614,958 B2 * | 11/2009 | Weston et al. | 473/62 |
| 7,721,209 B2 | 5/2010 | Tilton | |
| 7,722,458 B2 | 5/2010 | Walker et al. | |
| 7,749,089 B1 * | 7/2010 | Briggs et al. | 472/136 |
| 7,785,193 B2 | 8/2010 | Paulsen et al. | |
| 7,850,527 B2 * | 12/2010 | Barney et al. | 463/37 |
| 7,878,905 B2 * | 2/2011 | Weston | A63F 13/10 463/10 |
| 7,946,917 B2 | 5/2011 | Kaminkow et al. | |
| 8,091,026 B2 | 1/2012 | Wolff et al. | |
| 8,230,344 B2 | 7/2012 | Abujbara et al. | |
| 8,708,821 B2 * | 4/2014 | Barney et al. | 463/36 |
| 2002/0013174 A1 | 1/2002 | Murata | |
| 2002/0021288 A1 | 2/2002 | Schug | |
| 2002/0022998 A1 | 2/2002 | Onoue | |
| 2002/0042744 A1 | 4/2002 | Kohl | |
| 2002/0047020 A1 | 4/2002 | Dudek | |
| 2002/0065745 A1 | 5/2002 | De La Fuente | |
| 2002/0065579 A1 | 5/2002 | Tedesco et al. | |
| 2002/0077174 A1 | 6/2002 | Luciano et al. | |
| 2002/0107610 A1 | 8/2002 | Kaehler et al. | |
| 2002/0147640 A1 | 10/2002 | Daniels et al. | |
| 2003/0036425 A1 | 2/2003 | Kaminkow et al. | |
| 2003/0061098 A1 | 3/2003 | Meyer | |
| 2003/0073479 A1 * | 4/2003 | Wilson et al. | 463/16 |
| 2003/0097302 A1 | 5/2003 | Overhultz et al. | |
| 2003/0186739 A1 | 10/2003 | Paulsen et al. | |
| 2004/0001106 A1 | 1/2004 | Deutscher et al. | |
| 2004/0024642 A1 | 2/2004 | Sidlo et al. | |
| 2004/0033833 A1 * | 2/2004 | Briggs et al. | 463/42 |
| 2004/0077423 A1 * | 4/2004 | Weston | A63G 31/00 472/137 |
| 2004/0092311 A1 | 5/2004 | Weston et al. | |
| 2004/0103028 A1 | 5/2004 | Littman et al. | |
| 2004/0128197 A1 | 7/2004 | Bam et al. | |
| 2004/0133466 A1 | 7/2004 | Redmond | |
| 2004/0152520 A1 | 8/2004 | Shinoda | |
| 2004/0152521 A1 | 8/2004 | Shinoda | |
| 2004/0158489 A1 | 8/2004 | Rogers | |
| 2004/0220510 A1 | 11/2004 | Koullick et al. | |
| 2004/0230572 A1 | 11/2004 | Omoigui | |
| 2004/0235542 A1 * | 11/2004 | Stronach et al. | 463/6 |
| 2005/0051953 A1 | 3/2005 | Yamashita | |
| 2006/0030385 A1 * | 2/2006 | Barney et al. | 463/9 |
| 2006/0106488 A1 * | 5/2006 | Zito | 700/231 |
| 2006/0154726 A1 * | 7/2006 | Weston | A63F 13/10 463/37 |
| 2006/0272976 A1 | 12/2006 | Pinney et al. | |
| 2007/0066396 A1 * | 3/2007 | Weston et al. | 463/39 |
| 2007/0081197 A1 | 4/2007 | Omoigui et al. | |
| 2007/0101251 A1 | 5/2007 | Lee et al. | |
| 2008/0176648 A1 | 7/2008 | Zito | |
| 2009/0282093 A1 | 11/2009 | Allard et al. | |
| 2012/0131098 A1 | 5/2012 | Wood et al. | |

FOREIGN PATENT DOCUMENTS

| | | |
|---|---|---|
| JP | 2002245083 A | 8/2002 |
| JP | 2003208524 A | 7/2003 |
| KR | 1020110085122 A | 7/2011 |
| KR | 1020120050615 A | 5/2012 |
| KR | 1020120051210 A | 5/2012 |
| WO | 9718538 A1 | 5/1997 |
| WO | WO 01/12035 | 2/2001 |
| WO | 2006055510 A1 | 5/2006 |
| WO | 2014138352 A1 | 9/2014 |

OTHER PUBLICATIONS

MedVantx Aligns with Major Health Plans to Build the First Generic Delivery Network (received from MedVantx, Inc. Apr. 7, 2005).

Kazel, Robert, "AMN News Staff", Robot Rep Latest Tactic in Generics Push, http://www.amaassn.org/amednews/3005/0 1/31/bil20 131.htm, Jan. 31, 2005, 5 pages.

PCT/US2005/041251, International Application Serial No. PCT/US2005/041251, International Preliminary Report on Patentability mailed Feb. 9, 2012, Zito, Arthur, J., Jr., 30 pages.

PCT/US2005/041251, International Application Serial No. PCT/US2005/041251, International Search Report and Written Opinion mailed Apr. 3, 2006, Zito, Arthur, J., Jr., 8 pages.

Rawe, Julie et al., "Popping Pills Out of an ATM", http://www.time.com/time/archive,/preview/O, 10987,1 029873,00.html, Feb. 28, 2005, 4 pages.

EP05821081.6, "Communication Pursuant to Article 94(3) EPC for European Patent Application No. EP05821081.6", Apr. 8, 2009, 6 pages.

EP05821081.6, "Oral Proceedings Decision for European Patent Application No. EP05821081.6", Feb. 6, 2012, 16 pages.

EP05821081.6, "Summons to Attend Oral Proceedings pursuant to Rule 115(1) EPC for European Patent Application No. EP05821081.6", Dec. 9, 2011, 8 pages.

PCT/US2014/021067, "International Application Serial No. PCT/US2014/021067, International Search Report and Written Opinion mailed Jun. 27, 2014", Zito, J.Arthur, 12 pages.

PCT/US2014/021067, "International Application Serial No. PCT/US2014/021067, International Preliminary Report on Patentability and Written Opinion mailed Sep. 17, 2015", Zito, Arthur J., 9 Pages.

* cited by examiner

USER-SPECIFIC DISPENSING SYSTEM

CLAIM OF PRIORITY

This application is a continuation in part of U.S. Non-Provisional application Ser. No. 10/990,595 filed on Nov. 17, 2004.

BACKGROUND OF THE INVENTION

1. Field of Invention

This invention relates in general to systems and methods for on-site, automated dispensing of items to users based on user-specific information. The system and methods can also be applied to gaming devices and interactive amusement playfields in which a special feature is actuated and/or an item is dispensed based on user-specific information.

2. Description of the Prior Art

In general, the retail market continues to become more competitive. There are an increasing number of options for consumers in terms of where to shop and which items to purchase. At the same time, providing targeted samples to consumers is an effective method of marketing. Therefore, there exists a powerful need to direct consumers into appropriate store locations and/or to direct samples of products into the hands of a targeted consumer.

While promotional methods have existed for ages, e.g., sales coupons, targeted discounts, free items with purchase, no system or method has attempted an automated approach to targeted on-site sampling. To do so would require (1) pre-knowledge of the targeted consumer, also referred to as the "user" of the system, and (2) the actual dispensation of samples to said user based on that pre-knowledge. Such a system would differ from one that issues a coupon or other redeemable, such as a token, to a user based on user-specific information, in that said system would actually physically dispense the item to the user on-site, thereby removing the necessity of a redemption step.

Such a system would provide a novel method and system to provide automated, on-site sampling based on user-specific information. The system and method could incorporate RFID, bar code, or any other reader technology into an automated system that can be kept and maintained on a target site or maintained from a central site. Reader systems such as RFID tags, bar codes, and other conventional data reading methods are incorporated into a variety of devices ranging from monitoring systems to gaming devices. One example would be a grocery store chain issuing discounts to holders of a preferred customer card. The card may have information on it that is readable by a bar code reader. The system identifies the user by the information contained on the card and issues a discount, or tracks the consumers purchase history, and issues coupons based on said history. Another example is Bam et al.'s U.S. patent application Ser. No. 10/691,459 (Publication No. US 2004/0128197), which discloses an electronic promotion system that sends coupons to targeted consumers, the coupons tailored to the specific consumer's profile. The consumer then may redeem said coupons at some future time.

Another example of the prior art is Meyer's U.S. patent application Ser. No. 10/245,149 (Publication No. US 2003/0061098 A1), which discloses a system that encourages consumers to patronize a particular business by awarding a prize or a discount to randomly selected consumers. But the system disclosed in Meyer's patent application does not physically dispense a sample. Another drawback of this system is that an item provided may not meet the needs or desires of the actual user because the item provided is not customized to that user's individual characteristics or preferences. Such a system is not necessarily based on user-specific information but rather simply rewards consumers that have a card.

Thus, there is a need for a system that both physically provides the item on-site from the dispenser unit itself and one that dispenses an item that is user-specific based on the particular user's characteristics.

SUMMARY AND OBJECTS OF THE INVENTION

In general, the dispensing system of the present invention comprises a user-identifier, such as an RFID tag or a bar code, containing information associated with a user. The system also comprises a reader that is capable of reading the user-identifier. The system has a processor that is capable of executing instructions to actuate dispensing means that in turn dispenses an item or sample to the user. In this way, the system is designed to dispense an item that is appropriate for the user based on user-specific information.

In an alternate embodiment, the system is capable of conveying information associated with the items. In this alternate embodiment, the processor is capable of instructing an actuator to dispense items based on item-specific information. Item-specific information includes, but is not limited to, the number of items dispensed from at least one storage compartment or the weight of items remaining in at least one storage compartment.

In another embodiment, the invention comprises a system incorporated into a gaming device. Instead of or in addition to dispensing a sample, the system will actuate at least one gaming feature based on the information associated with the identified user. This embodiment is designed to actuate a gaming feature that is appropriate for the user based on the user-specific information or to provide free or extended play to the user based on user-specific information.

In another embodiment, the invention comprises a system incorporated into stations located throughout an interactive playfield. In this embodiment, the dispensing system may dispense items or information, or may activate or inactivate a feature of the playfield, based on the information on the user-identifier to facilitate play in the interactive amusement system.

All embodiments may be optimally coupled with any device that dispenses a service or item in exchange for currency or other monetary means, such as a credit card.

It is therefore an object in an example of the present invention to provide a system to physically dispense a sample item on-site to a user based on user-specific information.

It is a further object in an example of the present invention to provide a system that physically dispenses an item on-site to a user based on information related to the items remaining in the system.

It is also an object in an example of the invention to provide a gaming system that activates gaming features based on user-specific information.

It is a further object in an example of the invention to provide a system that activates features within an existing gaming machine based on user-specific information.

It is still a further object in an example of the invention to provide targeted automated sampling of items.

It is another object in an example of the invention to provide a system to encourage consumer traffic to a location by dispensing items based on user-specific information.

In another example, it is an object of the invention to provide an interactive amusement system that activates or inactivates features on the playfield based on user-specific information.

It is yet a further object in an example of the invention to provide an interactive amusement system that activates or inactivates features on the playfield based on information contained on the user-identifier.

In another example, it is another object of the present invention to provide an interactive amusement system that dispenses items that may be used immediately and/or in the future to facilitate play in the amusement system.

Other objects, features, aspects and advantages of the present invention will become better understood or apparent from the following detailed description, drawings, and appended claims of the invention.

DESCRIPTION OF THE PREFERRED EMBODIMENT

Figure 1:
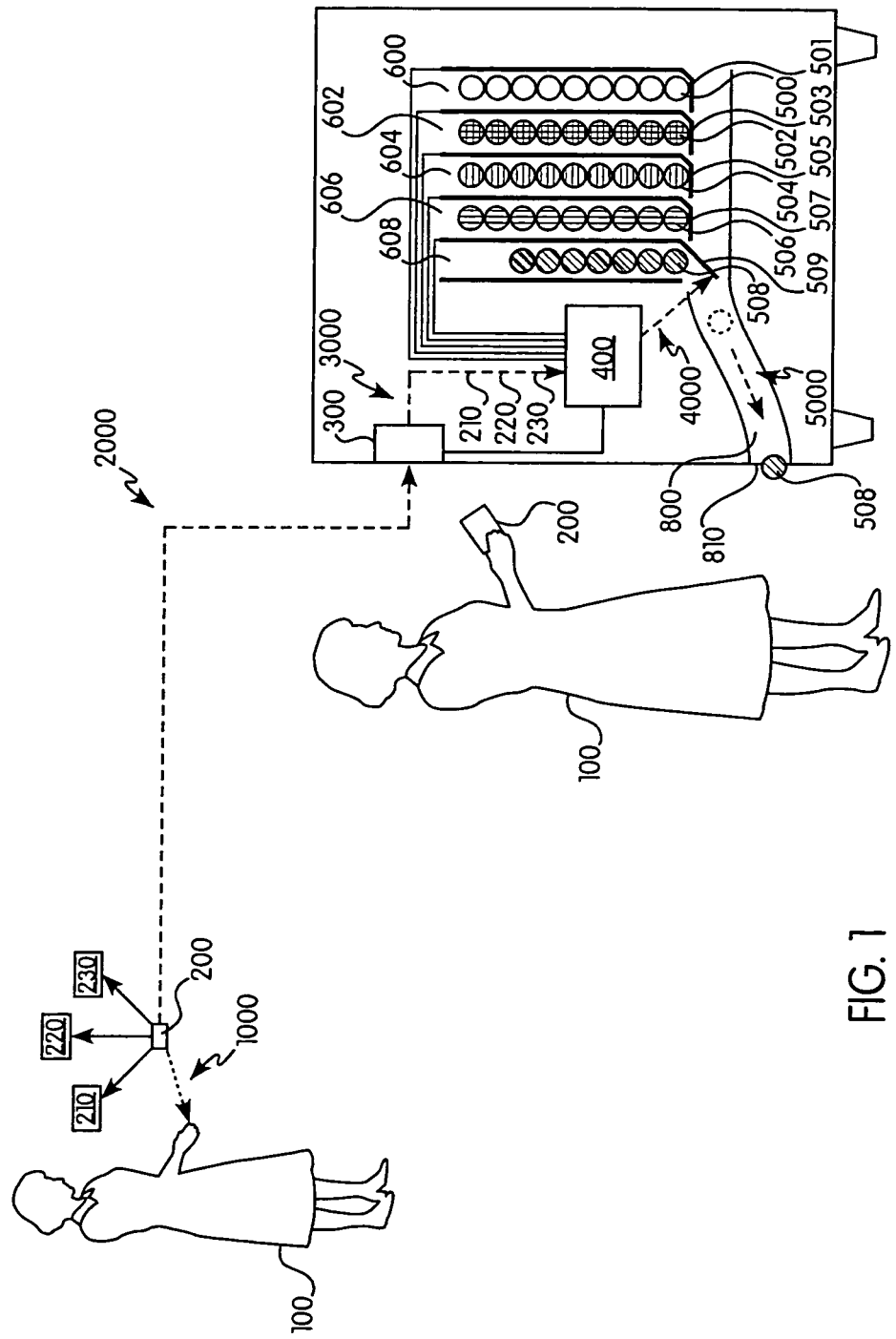
FIG. 1 is a schematic depiction of the user-specific dispensing system in an embodiment of the invention.

FIG. 1 shows a schematic depiction of an embodiment of the process and system for on-site dispensing of items or samples based on user-specific information. In this embodiment, the system is schematically represented as a vending-type machine dispensing items to a user, where the item is for examples a physical item such as a product, sample, game feature, or other object, or an intangible item such as a service, a game feature, or a multimedia experience. Where the item is a physical sample, it may be any shape, such as for examples spherical or cylindrical. The skilled artisan will appreciate, of course, that there are a multitude of types of vending machines, many of which have differing mechanical or electrical configurations and capabilities. Thus, this embodiment of the invention is in no way limited to vending-type machines represented in this schematic. The skilled artisan will also appreciate, of course, that the dispensed items need not be cylindrical or be limited to any shape. The items could be intangible, such as a music clip. Thus, an item can be a physical sample or a service. Another example of an item as a service would be the system dispensing multi-media clip, a shoe shine, a car wash, or the use of a locker in a gym facility. In another example where the item is a service, service can include entertainment that the user observes and/or participates in. Some of the other applications of the invention will become apparent from the schematic figures discussed below.

As shown in FIG. 1, a user 100 receives a user identifier 200. That step is represented as 1000. The way in which a user receives a card varies, but an example would be as follows: A vendor stationed at an event, for example, a sporting event, would solicit interested consumers and would gather information from the interested consumers. Such information could include the consumer's age, gender, sporting team or apparel preferences, location of residence, and any other such information selected or designated by the vendor. The vendor would issue the user a card that could be used with the system. In this example, the card would be a user-identifier 200. Skilled artisans will appreciate that the user-identifier 200 need not be a card, for example, the user-identifier 200 could be any physical holder of information and need not be limited to any size or shape. Further, the user-identifier 200 could be any information that is specific to a user 100, which is inputted into the system, for example, the user 100 could enter the user's phone number into the system. Still further, the issuer of the user-identifier 200 need not necessarily be a vendor as is currently understood by the ordinary and accustomed meaning of "vendor." The user-identifier 200 comprises readable information that is specific to or is associated with the user. The readable information may be updated at least once or periodically by the user or the issuer, by the user's usage history, or based on a survey or questionnaire answered by the user subsequent to use of the user-identifier. As stated above, said user-specific information may include gender, name, address, age, athletic preference, food preferences, music preferences, etc. FIG. 1 schematically represents such preferences as 210, 220, and 230. User-specific information 210, 220, and 230 on the user-identifier 200 may be in the form of a bar code or RFID information, but is not limited as such. User-specific information also includes information that a user is simply authorized to receive a sample. Therefore, information on a user-identifier that instructs the system to simply dispense an item is user-specific information.

Another step of the invention is represented by 2000. In this step, the user 100 presents the user-identifier 200 to the system. The system comprises a reader 300 capable of reading the coded information off of the user-identifier 200. In one example of an embodiment, the reader 300 is an RFID reader capable of reading data on a card that corresponds to the user's 100 age 210, gender 220, and soft drink preference 230. The reader 300 sends the user-specific data to a processor, the step being represented by 3000. In step 4000, the processor 400 is capable of processing the inputted user-specific data in order to instruct the system to dispense an item to a user, that item being selected based upon the user-specific data. The step of dispensing is represented by 5000. FIG. 1 depicts the item being dispensed as 508.

In some of the embodiments of the invention where the instructions are software, the software contains coded instructions, which translate the user-specific data into mechanical action of the system, specifically, mechanical actions of the dispensing means 501, 503, 505, 507, or 509. Software can also log the activities in a file. The software can validate whether the user-identifier 200 is authorized for activity. It can determine, for example, whether the user history warrants an item to be dispensed. The software can determine which type of item will be dispensed and log a tag number along with a time stamp and activity type to a file. A control code tag is able to retrieve the file and reset the system. Skilled artisans will appreciate that the invention is not limited or dependent upon any type of computer system, operating environment, architecture, or required to have a conventional computer to operate. In other embodiments of the invention, it is possible to reduce the software routine to a dedicated chip, and remove the typical computer components from the invention completely.

The step of the reader 300 being provided with the user-specific information 210, 220, and 230 of the user-identifier 200 to the processor 400 is represented by 3000. Once the processor accepts the user-specific data 210, 220, and 230, it executes an instruction to actuate a dispensing means 500, 502, 504, 506, 508 based on set instructions.

In this embodiment, the system has at least one or optionally multiple compartments 600, 602, 604, 606 and 608, each of which stores a plurality of items to dispense. One such item is represented as 508. As described above, the item may be any type of item, including for examples a physical sample, a service, or a gaming feature, so long as the item is dispensed based upon user-specific data. However, presently such items may include toys, prizes, candy, soda, athletic gear, towels, etc. In the example shown in FIG. 1, each item is schematically represented, and each item is stored in its respective storage compartments 600, 602, 604, 606, and 608. In the preferred embodiment, the items meet a pre-selected set of characteristics appropriate for a user. That is, for example, if the user-specific information includes soda or candy preference, a soda or a candy item would be dispensed that corresponds to the preference.

Related to this aspect of the invention, other embodiments of the invention comprise dispensing an item based on whether the user 100 meets the pre-selected criteria selected by an entity wishing to promote certain goods. For example, the system could be located in a retail area such as a grocery store. The system may contain samples of items typically found in the store such as after-shave, samples of a skin-toning product, and samples of vitamin supplements respectively. The pre-selected criteria may define that (1) males under forty five years of age are to receive after-shave samples; (2) females under forty-five years of age are to receive samples of the skin toning product; and that (3) all individuals over forty-five years of age will receive the sample of vitamin supplements. A twenty-nine year old male presenting his user-identifier to the system will cause the system to dispense to him a sample of after shave. In this way, the invention can provide for focused automated sampling, which is an important marketing tool. By providing the user 100 with a customized item the invention can also drive consumer traffic to a location, which in this example is a grocery store. In this embodiment, the steps of presenting 2000 the user identifier, reading the user-specific information 3000, and processing 4000 are the same as described above.

Dispensing 5000 is another aspect of the invention. The skilled artisan will appreciate that any conventional dispensing means can be used. Since the invention is not limited to any particular mechanical or electrical specifications, the dispensing means will depend largely on the type of unit the system is embodied within. In one embodiment, the dispensing means is a flange that is activated by a solenoid. The reader reads information contained on the user-identifier and sends the information to the processor, which processes instructions to send an electrical signal to the solenoid. This electrical signal charges a coil in the solenoid, which in turn pushes a rod mechanism in the solenoid to open the flange to dispense an item from the respective storage compartment 600, 602, 604, 606, 608, for example into a dispensing chute 800, out of the opening 810, and on to the user 100. Alternate embodiments will use shooting solenoids to drive the sample into a dispensing chute ultimately accessible by the user.

In an embodiment, machines or devices incorporated into the user-identifier 200 and dispensing system can be activated in series to encourage users to visit different retail locations, or to experience different gaming machines. For examples, there may be a different video game that is highlighted each day in an arcade, or a different slot machine that is highlighted each day in a casino, and the machine then reads the user-identifier 200 presented by user 100 to determine if the user 100 is authorized for use on the highlighted machine, and if so, which if any features of the highlighted machine should be activated for user 100 based on the information stored on the user-identifier 200.

In other embodiments, the invention has dimensions that are suitable for a retail shelf, for example, on the confectionery shelf of a convenience store; however, the size dimensions of the units are variable and could easily be adapted to any environment whether it be retail or service. The system could also be freestanding in a public place.

In another embodiment, the system could be installed or made a part of a jukebox type machine, or a machine that otherwise dispenses music or multimedia presentation. In such a system, the user-identifier would be presented to a reader on the system. The user-specific information would be sent to the processor. The processor would instruct the system to "dispense" or otherwise play a multimedia or music clip based on the user-specific information.

Figure 2:
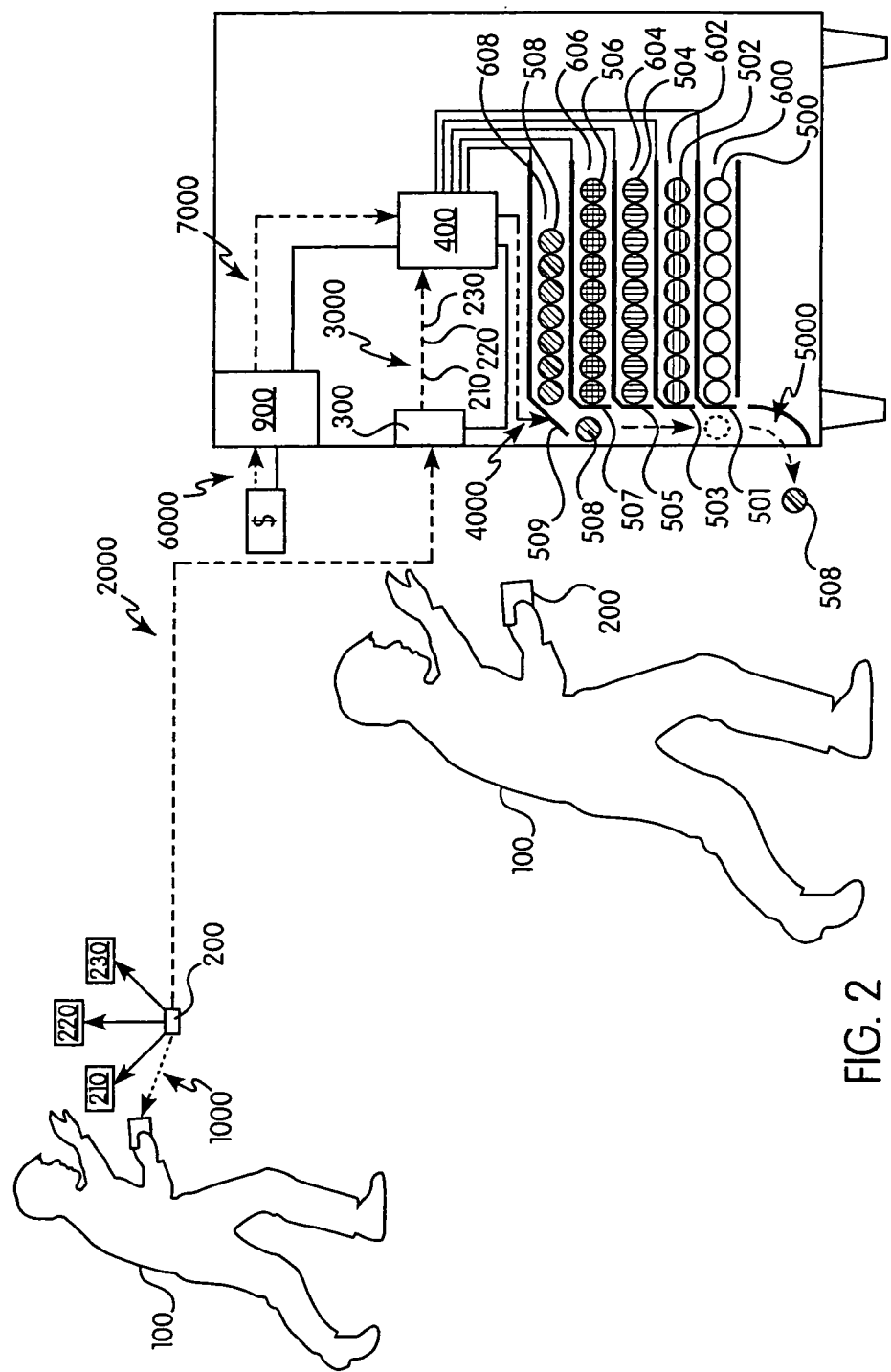
FIG. 2 is a schematic of another embodiment of the invention.

In an alternate embodiment shown in FIG. 2, the invention could be a dispensing or vending type system of the conventional type where the system is configured to accept payment including for examples currency, credit, or debit, and to dispense an item that is appropriate for the user based on user-specific information, the item being paid for by the user. A typical example of this would be a soda vending machine. In this alternate embodiment, the system contains a currency accepting means 900. The processor can contain and/or execute instructions to only activate the system if currency accepting means indicates to the process that the user 100 has paid for one of the items 508. For example, a user could purchase a soda by inserting currency into the currency acceptor 900 (the step represented as 6000), which would be communicated to the processor 400, represented by step 7000. In some embodiments, the processor 400 executes instructions to output a prompt to the user. In a preferred embodiment, the prompt would be a graphical display indicating to the user to present his or her user-identifier 200. The system then reads the user-specific information 210, 220, and 230, and optionally, the user's 100 immediately previous purchase choice, and instructs the dispensing means (508 for example) to dispense a separate item to the user 100 based on the selected criteria for that user type and/or the user's 100 selection.

Other embodiments of the invention include a system to distribute items to a member of a health club, where the distributed items are chosen based on pre-selected athletic interests of the member, such as providing tennis balls to a member who has previously indicated an interest in playing tennis. Alternatively, the member of the athletic club may have purchased a premium service. The information regarding the premium service would be contained on the user-identifier and the system would dispense items based on the member's status and/or preferences.

Another embodiment comprises a system to distribute meals to school students based on pre-selected menu preferences.

Another embodiment comprises a system to dispense or distribute pharmaceuticals or over the counter medications based on user-specific information contained or stored on the user-identifier 200.

In another embodiment, the user-identifier is used in conjunction with an automatic sports machine, such as for example, an automatic baseball or soccer machine, in which the level of difficulty of play is adjusted based on the user's skill level, which is coded or stored on user-identifier 200.

The skilled artisan will appreciate that the components of the system can be used with any vending machine, amusement machine, slot machine, or any device that dispenses an item or service.

In another embodiment, the system dispenses items based on said user-specific information and item-specific information in combination. In this embodiment, the system dispenses at least one item based on information associated with the items in at least one of the storage compartments. This item-specific information includes, but is not limited to, the number of items dispensed from at least one storage compartment, the number of items remaining in at least one storage compartment, or the weight of items remaining in at least one storage compartment. This sample-specific information is conveyed to the processor, which in conjunction with the programmed instructions is capable of translating the information into mechanical actions of the dispensing means as described above. In an example, items are dispensed to select users 100, and as the quantity of these items decreases, the selection criteria for users 100 to receive the items become more stringent so that some users no longer qualify to receive the item or receive a substitute item.

Another embodiment of the invention is utilized in a gaming device. A gaming device according to the present invention incorporates all or some of the elements described in the embodiments above, except that the primary "item" being "dispensed" is a gaming feature. Therefore, in this embodiment of the invention, the "dispense" is to be understood as the activation of a gaming feature.

The user-identifier, reader, and processor are the same as those described above in FIG. 1 except that in this example system, the processor executes programmed instructions to translate the user-specific information to activate at least one gaming feature based on user-specific information stored on user-identifier and read by reader. Activated gaming feature is appropriate for user based on user-associated information. Activation of gaming feature includes deactivation of the gaming feature. The instructions, which can be encoded in software or embedded in a chip in the processor, are capable of validating whether the user-identifier is authorized for activity, determining history of use of the gaming system by user, and determining if and which gaming feature 575 should be activated. In an embodiment, there is a means to maintain a log of information, including the user-identifier and user's usage history, such as time, points scored, and what gaming feature was activated. For example, the means to maintain information may be instructions in conjunction with computer memory means. Any processor known to those skilled in the art may be used in the present invention without departing from the scope of the invention.

Figure 3:
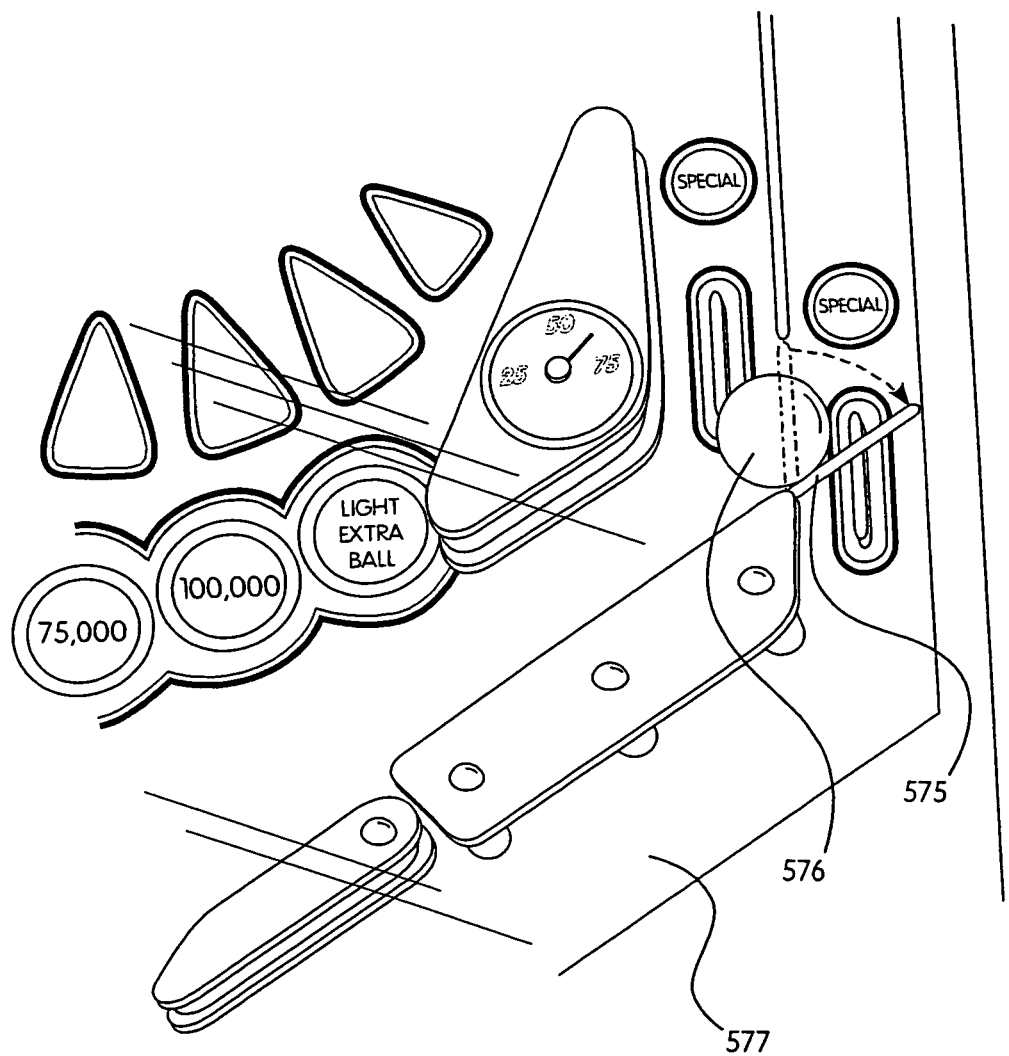
FIG. 3 is depiction of one embodiment of the invention incorporated into a gaming device.

In FIG. 3, the system is shown in conjunction with a pinball machine. The machine's level of play difficulty or winner reward may be adjusted by user-specific information. A close-up view of the activated gaming feature 575, which is a gate in this example, is shown. Gaming feature 575 may be a feature that is not typically activated until user completes a sequence of flipper lane and ramp spinner switches. By activating gaming feature 575, the system provides easier play for a new or young user by blocking the outlane 577 where the pinball 576 could be lost. In other examples, the gaming system provides free or extra play to a user based on user-specific information.

Another example of the system involves video games. In this example, a user of the system may present her card to a video game having the system incorporated therein. The user could then be awarded specific advantages in the video game based on the user-specific information contained on her card.

In some embodiments, the gaming feature that is activated is a free game on the system. The gaming feature could also be an adjustment of the threshold necessary to reach a new level of the game, to have a feature activated, or to obtain a re-play of the game.

In another embodiment, the claimed system is incorporated into an interactive amusement system that generates unique entertainment for users based on information stored on the user-identifier 200, including user-specific information and/or playfield information, where the playfield is the area in which the user interacts with the user-specific dispensing system and features of the playfield, and where playfield information includes, but is not limited to, the number or types of items or information previously dispensed to user 100. The playfield may be either a physical, tangible area, or it may be a conceptual or virtual area. The interactive amusement system according to the present invention incorporates all or some of the elements described in the embodiments above, except that the primary "item" being "dispensed" 508 may be an item that can be used in the claimed interactive amusement system, activation or inactivation of a feature of the playfield comprising the interactive amusement system, or provision of information, service(s), or a feature(s) that facilitate(s) play in the interactive amusement system.

The interactive amusement system is comprised of an amusement area 700 and at least one station 750 located therein. In an example, the amusement area 700 comprises a playfield 715 positioned between an entrance 705 and an exit 707. The playfield 715 is an amusement or entertainment area that has at least one feature such as walls, floors, doors 754, stairs 756, levels or stories 758, obstacles, tools for use in the interactive amusement system, or information or tools such as a map to assist a user 100 in the amusement system, for examples. Features may also include a service, such as turning on or off lights or music, or providing video of another player or area in the playfield. In an example, the user 100 may interact with playfield features.

Figure 4:
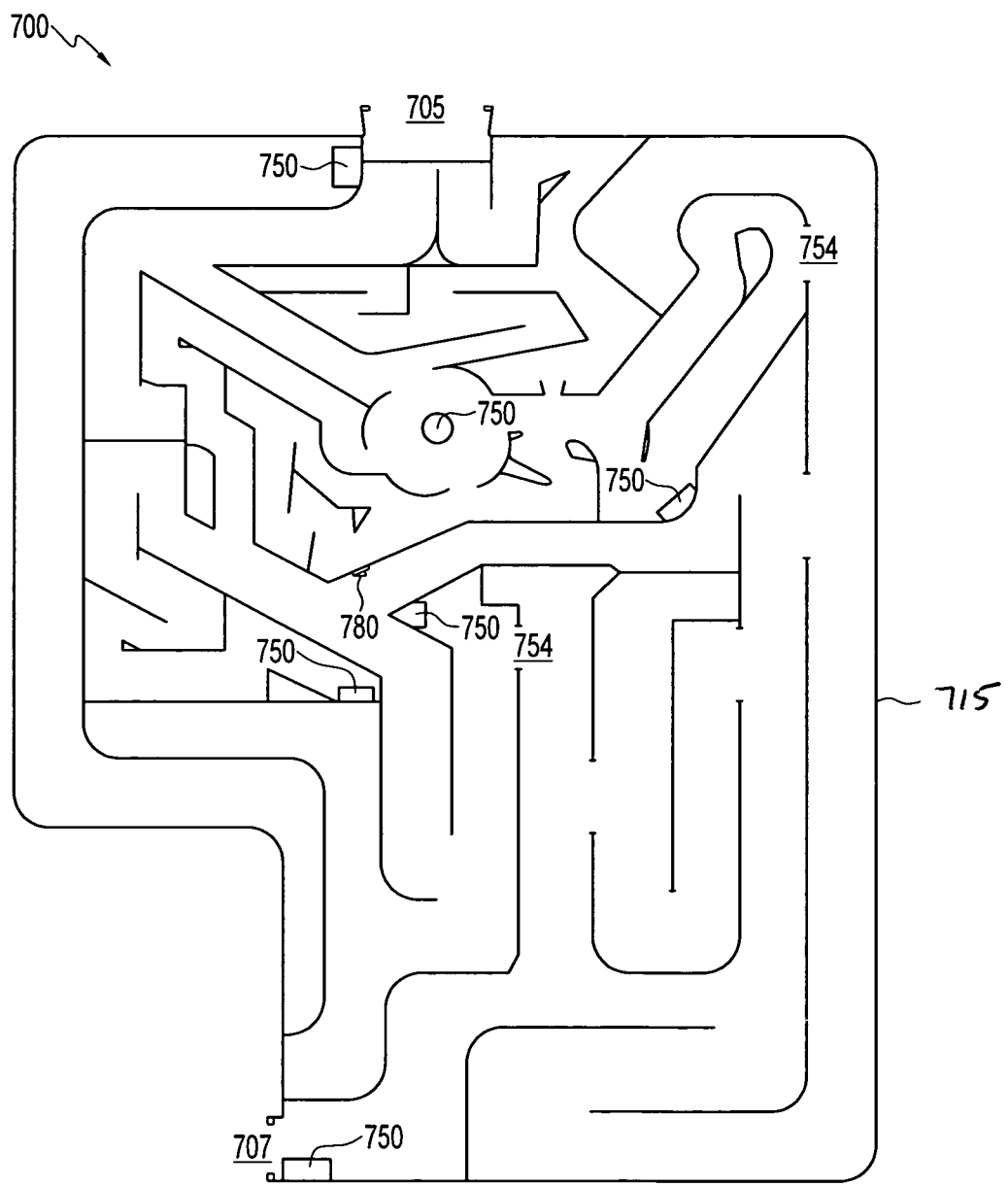
FIG. 4 is an example of an embodiment of the invention incorporated into an interactive amusement system where the playfield is a maze.

In an embodiment, at least one feature of the playfield 715 is capable of being activated or inactivated based on information stored on the user-identifier 200. In an example, activation or inactivation of a feature may give a user an advantage over other users, or may adjust the level of difficulty or challenge of the interactive amusement system. The playfield has at least one level 758 and may have multiple levels 758*a*, 758*b*, 758*c*. In a preferred embodiment, the features of the playfield 715 can be configured or adjusted to create a plurality of configurations so that, for example, repeat users are presented with a new or unique experience each time they participate in the interactive amusement system. For example, the system can account for the user 100 and determine whether to adjust or repeat the playfield experience, such as by maintaining or eliminating features based on information stored on user-identifier 200. In an example, the user's 100 play history (demographics, score, or playfield information), stored on the user-identifier 200, may determine the configuration of the playfield 715. For example, the playfield features may be adjusted to alter the level of difficulty of play so that the playfield 715 is easier for a younger child or a less experienced user than for an older or more experienced user. FIG. 4, described in more detail below, shows an example of an interactive amusement system in which the amusement area 700 is a maze. In other examples, the interactive amusement system 700 is an obstacle course, a building, a vessel, a jungle, or a battleground.

The interactive amusement system 700 further comprises at least one station 750 located within the amusement area 700. Each station 750 incorporates the claimed user-specific dispensing system, described in detail above. In an example, stations 750 are located at the entrance 705 and the exit 707, and there is at least one station on the playfield 715.

The user-identifier 200 is generally the same as that described above in FIG. 1 except that in this example system, the user-identifier 200 comprises user-specific information 210, 220, 230 and/or playfield information. As described above, in an example, the user-specific information is associated with a user 100, such as, for example, demographic information about the user, the user's play history, or the user's scores in the interactive amusement system. In another example, user-specific information is associated with a group of users, such as for example, demographic information about the group, including the number of members of the group, the gender(s) of the group members, and/or the age range of group members. User-specific information may also include user preferences, such as character roles that user 100 prefers to play in the interactive amusement system 700. In yet another example, the information is playfield information associated with the playfield 715, including information about character roles of characters in the interactive amusement system or about the configuration of the playfield 715. In an example, the user 100 is assigned a character role based on the information about the user stored on the user-identifier 200. An item that is appropriate for user 100 is dispensed based on user-specific 210, 220, 230 and/or playfield information.

The reader 300 and instructions are the same as those described above in FIG. 1. In an example, instructions are capable of validating whether the user 100 is authorized for play in the interactive amusement system based on the user's demographics or history of use or play in the interactive amusement system, for examples. Instructions may also determine which, if any, features of the playfield should be activated. The processor 400 executes programmed instructions to translate the user-specific or playfield information to dispense an item 508 for use in the interactive amusement system and/or to activate at least one feature based on information stored on the user-identifier 200. Activation of a playfield feature may include deactivation. For example, a door 754 may be locked when the user-identifier 200 indicates that the user 100 is a skilled, experienced, or repeat user, to increase the level of difficulty to make the interactive amusement system more challenging.

In an example, the instructions in conjunction with computer memory means also maintain a log of information, including the user-identifier 200 and user's 100 usage history, such as time spent playing in the interactive amusement system, points scored, what playfield feature was activated, or what items were dispensed. In an example, the user 100 scans the user-identifier 200 at the exit 707 of the playfield so that the log of information can be recorded on the user-identifier 200 to be stored until the user returns to the interactive amusement system or for the issuer or vendor records, marketing data, analysis, or other purpose. Any processor 400 known to those skilled in the art may be used in the present invention without departing from the scope of the invention.

The dispensing means may be the same as that described in FIG. 1. In an example, there is at least one storage compartment 600 at each station 750 which stores a plurality of items to dispense 508. The items 508 may be for use in the interactive amusement system and/or they may be for the user 100 to keep, such as for example memorabilia of the interactive experience. For another example, a key to unlock a secret passageway may be dispensed based on information on the user-identifier 200. In an alternate example, the dispensing means dispenses an activated or inactivated feature, such as a door 754 or passageway. For example, the activated or dispensed feature may be one that is not usually dispensed until a user 100 achieved a minimal score. By dispensing the feature, the system provides easier play for a new, inexperienced, or young user, which may give the user advantage by enabling the user 100 to reach his destination faster or with fewer obstacles. Likewise, features can be dispensed to increase the level of challenge or to provide varied levels of play or other combinations of play depending on the user-specific information and the issuer or vendor.

In a preferred example, the plurality of stations 750 are interlinked to affect each other. For example, when an item is dispensed 508 by one dispensing means at one station 750, other stations are coded not to dispense that same item to the same user. In another example, the stations 750 are interlinked to record a user's 100 score as she moves through the interactive amusement system. In this way, the user's history can be recorded as the user plays in the interactive amusement system to optionally change the features of the system during play, or the history can be used to determine the playfield configuration the next time the user plays in the interactive amusement system.

In an example, standardized scripts can be used, with gaps left in the scripts so that the actions of each user in the game of the interactive amusement system can be inserted therein. The insertions can be programmed according to the information stored on the user-identifier 200. In an example where there is a standard script for a "cop and robber scenario," a first user 100 is assigned a role of a policeman and a second user 100 is assigned the role of a jewel thief. Each user's 100 assigned role is stored on that user's user-identifier 200. The assigned role may be selected by the user 100 or may be assigned to the user 100 based on user's demographics. The information contained on the user-identifier, including demographic information and information about the assigned role is read by user-identifiers located at stations 750 throughout the playfield 715 to determine the user's 100 access to information or to activate or deactivate playfield features.

The interactive amusement system may further comprise a means for recording 780 a play session in the interactive amusement system, such as a video camera that may be mounted in the playfield 715 or in a viewing area (not shown) for viewing the playfield 715. The recording may be DVDs, photographs, customized books, multi-media, etc. Recordings may be used in the interactive amusement system and/or recordings may be kept by the user 100 as memorabilia of the experience. In examples, the recording can be merged to place the user 100 into scenes with other players. At any time during the adventure, these clips can be joined to create an existing artwork such as written books, pictures, movies, dramatic scripts, or video games.

In an alternate embodiment, additional users may participate remotely, such as for example through the internet or from a seated reception area. In an example, user-specific or playfield information, or a combination thereof, is used to create a scenario in the interactive amusement system, and then remote users further control at least one of the features of the playfield 715 to control and decide the challenge(s) faced by users 100 in the playfield 715.

FIG. 4 shows an example of the interactive amusement system in which playfield 715 is a maze. There is an entrance 705 and an exit 707, and a station 750 is located at each to record, for example, when a user 100 enters and exits the playfield 715. Stations 750 capable of reading user-identifier 200 are located throughout the playfield 715, the stations 750 being linked to doorways 754, which are features of the playfield 715. In an example, user-identifier 200 contains information about user 100 to indicate that user 100 is an experienced user, so that doorways 754 are closed, making it more difficult for user 100 to traverse through the maze. There is a recording means 780 mounted therein to record play on the playfield 715.

Figure 5:
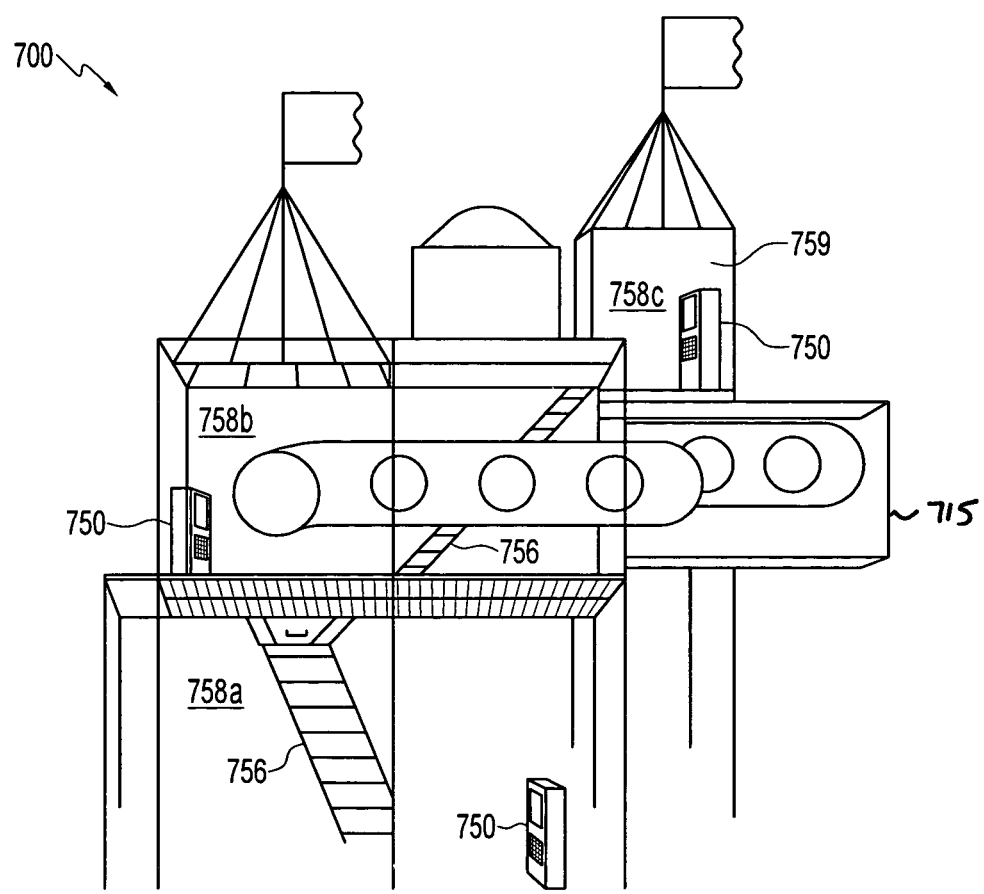
FIGS. 5 and 6 are examples of embodiments of the invention incorporated into an interactive amusement system where the playfield is a multilevel playground.
Figure 6:
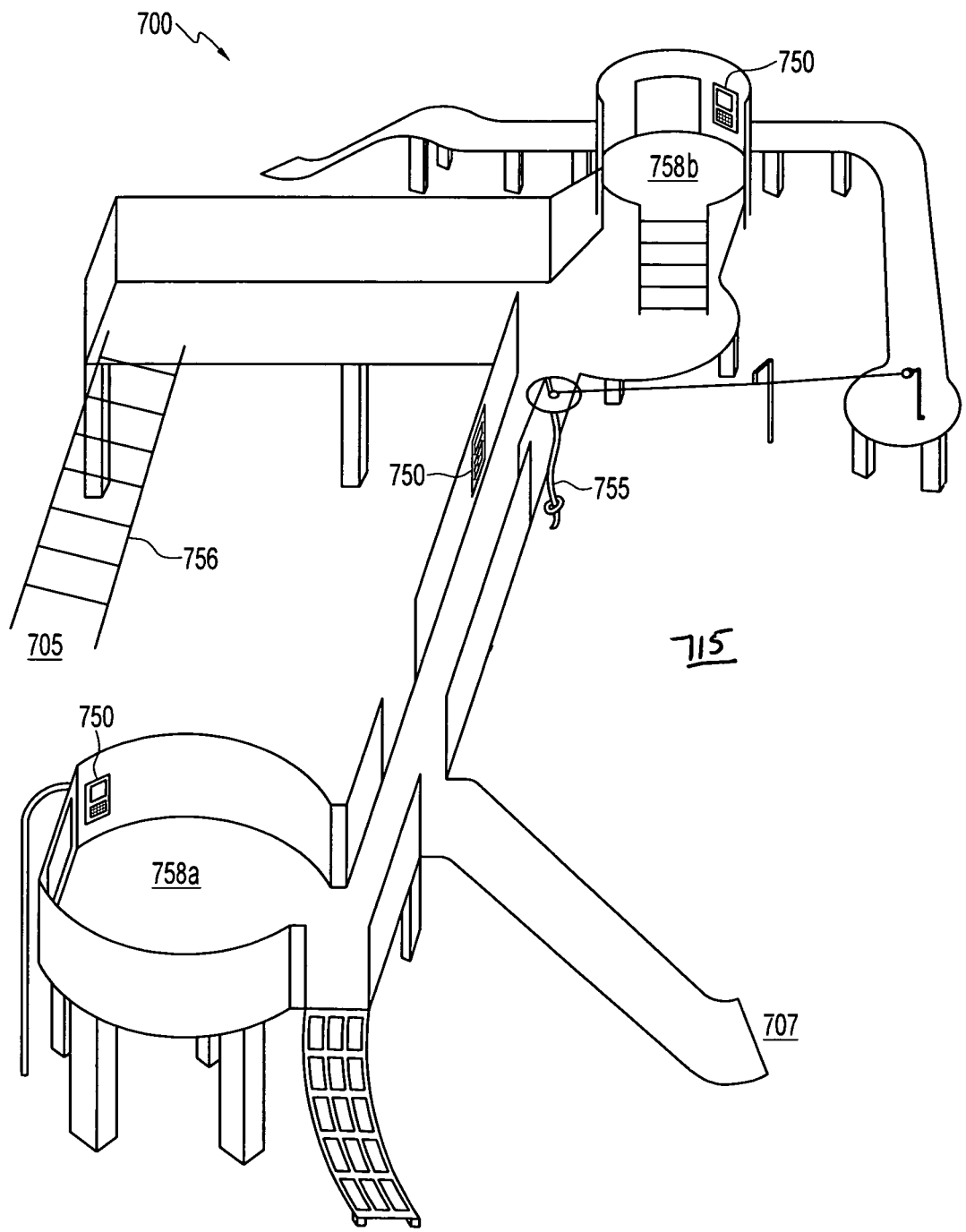

FIGS. 5 and 6 show examples of the interactive amusement system in which playfield 715 is a multilevel playground. In FIG. 5, a station 750 is located on each level 758 of the playfield 715. Stairs 756 connect the various levels 758. In an example, access to a tower 759 is granted based on information contained on the user-identifier 200. FIG. 6 also shows a multi-level playground that includes stations 750 throughout the playfield 715, stairs 756, and a rope 755 for access from one level 758 or platform to another. In an embodiment, each station 750 dispenses toys based on information contained on user-identifier 200.

Figure 7:
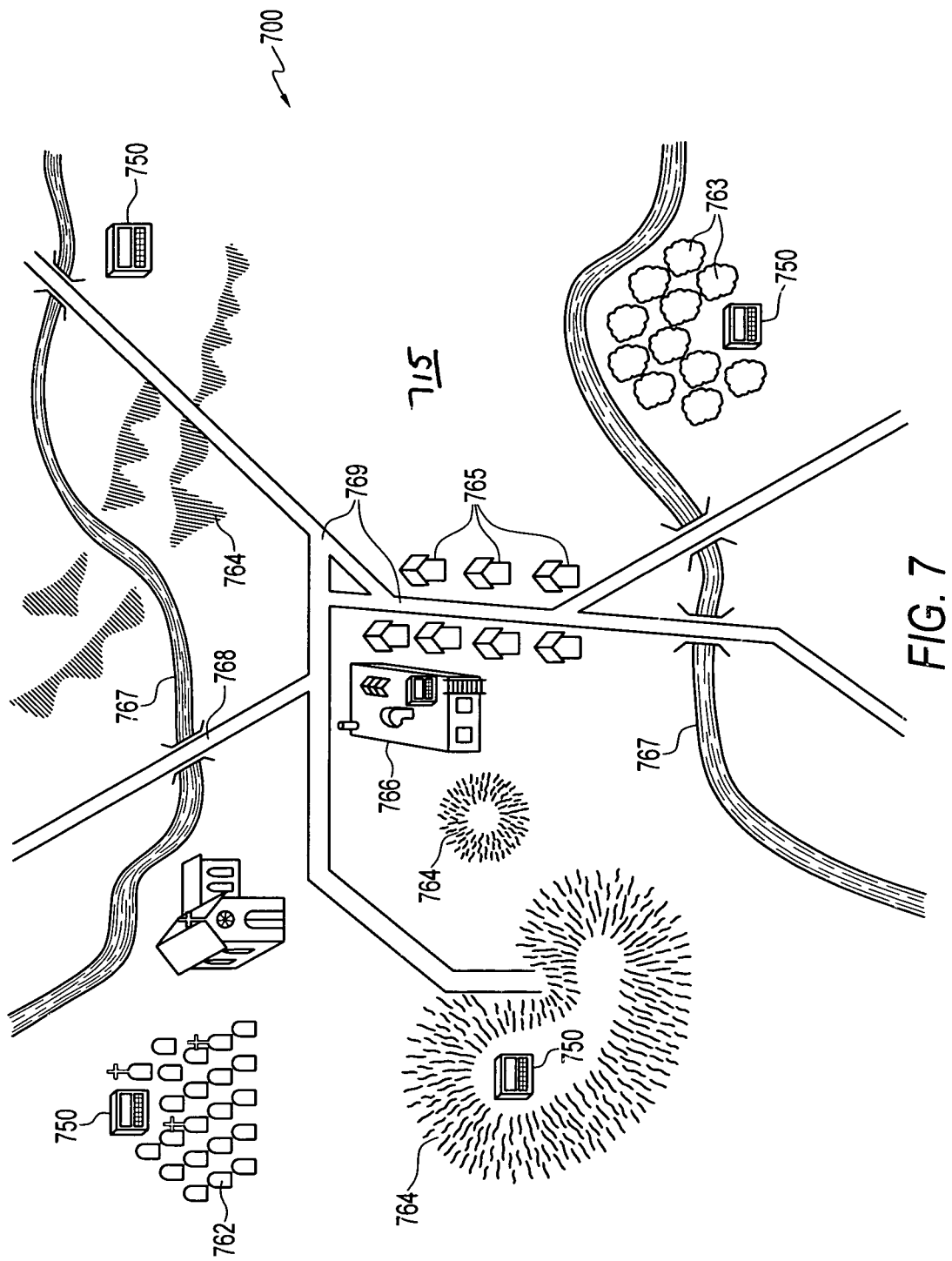
FIG. 7 is an example of an embodiment of the invention incorporated into an interactive amusement system where the playfield is an outdoor simulation area.

FIG. 7 is an example of an embodiment of the invention incorporated into an interactive amusement system where the playfield 715 is an outdoor simulation area that may be used for training SWAT team members or for battle reenactments, for examples. In an example, users 100 who achieve control of an area within the playfield receive ammunition or supplies from the dispensing means 500 located at each station 750 positioned on the playfield 715. In an example, the amount or type of ammunition dispensed is based on user-specific information, playfield specific information, or a combination thereof. In this embodiment, playfield features include a cemetery 762, trees and shrubs 763, high grass 764, houses 765 and office buildings 766, bodies of water 767, and bridges 768 and roadways 769.

In the examples shown in FIGS. 4-7, as described above, the user-identifier 200 can adjust the level of difficulty of the playfield maze based on user-specific information 210, 220, 230, user's 100 history or scores, or the playfield information, such as roles selected by each user 100. In examples, the users 100 may be individuals or a group of individuals, and there may be several groups competing against each other. As described above, the stations 750 on the playfield 715 dispense items or services to each user or group of users based on information stored on the user-identifier 200. The stations may be linked, as described above, so that as the user or group of users move through the playfield 715 the dispensation of items or services is based upon earlier performance in the playfield 715, for example, with a superior team receiving bonus items or bonus points.

In an alternate embodiment, the invention could be configured to accept payment 900, as described in FIG. 2 above. In this alternate embodiment, the system may be configured to provide access to the playfield 715, dispense an item 508 for use in the playfield 715, and/or activate a feature on the playfield 715. In yet another embodiment, the described interactive amusement system may be configured for use with the retail adaptations described above. For example, it is established through cross-marketing and use of visits and demographic variables. For example, the interactive amusement system encourages players and/or retail consumers to visit a retail location by, for example, awarding prizes at a retail dispenser or otherwise encouraging consumer traffic at the retail location.

In another embodiment, the user-identifier and dispensing system of the present invention is adapted to be a research or survey tool. User 100 is presented with a survey or a set of questions to answer, and the user's answers or feedback are stored on user-identifier 200 or are used to create information about user 100 that is stored on user-identifier 200 so that when user 100 presents user-identifier 200 to a reader 300 items 508, samples, or services that are user-specific are dispensed to user 100. In an example, the survey or questions relate to a dispensing system that includes user-identifier 200, so that user's 100 responses to the survey may be stored on user-identifier 200 to affect the items or services that are dispensed to user 100 in subsequent experiences or play with the user-identifier and dispensing system, such as, for example the gaming device or interactive amusement system. In an embodiment, the issuer or provider of the user-identifier 200 has access to the user's feedback or survey answers so that the issuer can use the information for market research. In another embodiment, the user's feedback or survey answers may be used to update the information stored on the user-identifier 200 at least once or periodically.

In yet another embodiment, the user-identifier and dispensing system of the present invention can be combined with more than one of the embodiments described above, so that, for example, there is a system that includes a user-identifier and dispensing system in combination with a gaming device that is connected to an interactive amusement system.

While the foregoing has been set forth in considerable detail, it is to be understood that the drawings and detailed embodiments are presented for elucidation and not limitation. Design variations, especially in matters of shape, size and arrangements of parts may be made but are within the principles of the invention. Those skilled in the art will realize that such changes or modifications of the invention or combinations of elements, variations, equivalents or improvements therein are still within the scope of the invention as defined in the appended claims.

What is claimed is:

1. An interactive amusement system, the system comprising:
    a reader configured for reading a user-identifier associated with a user and associated with user-specific information of the user, wherein the user-specific information existed prior to the user's interaction with the system;
    a feature of a playfield; and
    a processor in communication with the feature and the reader, the processor operable to execute coded instructions to interpret the user-identifier and configure the feature in response to the associated user-specific information such that the playfield is configured specifically for the user, wherein to configure the feature based upon the user-specific information includes activating the feature such that a difficulty of play is appropriate for the user
    wherein the user-specific information is one of the user's name, address, age, gender, personal characteristic of the user, physical status of the user, legal authorization, role of the user within a group or team wherein the group or team existed prior to the user's interaction with the system, a position played or preferred prior to the user's interaction with the system for a sport, and a combination thereof.

2. The system of claim 1, wherein the feature is at least one of an entrance or exit.

3. The system of claim 2, wherein the feature includes at least one station.

4. The system of claim 3, wherein a position of said at least one station at least partially defines a boundary of the playfield.

5. The system of claim 3, further comprising a dispensing device within the station.

6. The system of claim 1, wherein configuration of the feature includes activation or deactivation of the feature.

7. The system of claim 1, wherein the feature is operable to serve two or more users.

8. The system of claim 1, further comprising a payment accepting device coupled with the processor, the coded instructions operable to activate the feature in response to the user inserting an appropriate amount of currency into the payment accepting device.

9. The system of claim 1, wherein the feature comprises at least one of:
   a wall;
   a door;
   a passageway;
   a stairwell;
   a tunnel;
   a tool for use in the interactive amusement system;
   information for use in the interactive amusement system;
   a ramp;
   a ball;
   a sports object;
   a service.

10. The system of claim 1, wherein the feature is a dispensing device.

11. The system of claim 10, wherein the dispensing device is operable to dispense a sports object.

12. The system of claim 11, wherein the feature is how the sports object is dispensed.

13. The system of claim 12, wherein the sports object is a baseball.

14. The system of claim 1, wherein the processor is operable to execute the coded instructions to actuate the feature based on object-specific information.

15. The system of claim 1, further comprising a computer memory in electronic communication with the processor to maintain a log of information relating to play in the interactive amusement system.

16. The system of claim 15, wherein the computer memory is operable to store information relating to the user, the playfield, and the configuration of the features for the user.

17. The system of claim 1, wherein the at least one station comprises at least two stations that are electronically interlinked.

18. An interactive amusement system, the system comprising:
   a reader configured for reading a user-identifier associated with a user and associated with at least one personal characteristic of a user, wherein the personal characteristic existed prior to the user's interaction with the system;
   a feature of a playfield; and
   a processor in communication with the feature and the reader, the processor operable to execute coded instructions to interpret the user-identifier and configure the feature in response to the characteristic such that the amusement is more appropriate for the user
   wherein the at least one personal characteristics of the user is one of the user's name, address, age, gender, personal characteristics of the user, physical status of the user, legal authorization, role of the user within a group or team wherein the group or team existed prior to the user's interaction with the system, a position played or preferred prior to the user's interaction with the system for a sport, and a combination thereof.

19. The system of claim 18, wherein a provider of the system has access to user-feedback.

20. The system of claim 18, wherein the user-specific information is periodically updated by at least one of the following:
   the user;
   a provider of the system;
   a user-feedback.

21. The system of claim 1, wherein more than one feature is activated in a series based on the user-specific information.

22. The system of claim 1, wherein the feature is a free play of the system.

23. The system of claim 1, wherein the user-specific information is a characteristic.

24. The system of claim 1, wherein the user-specific information is included in a profile.

25. The system of claim 1, wherein the user-identifier is read by the reader such that the user-specific information associated with the user identifier is accessed from a computer memory by the processor.

26. The system of claim 1, wherein the configuration of the feature includes an adjustment to a dispensation.

27. The system of claim 26, wherein the dispensation includes dispensation of a sports object.

28. The system of claim 26, wherein the dispensation includes dispensation of a baseball.

29. The system of claim 1, where the configuration is controlled by a user other than the user associated with the user-specific information.

30. The system of claim 1, wherein the processor executes the instructions to present the user with a menu based on the user-specific information, the menu operable to configure the feature.

31. The system of claim 1, wherein the system is connected to the Internet such that the user can interact with the system.

32. The system of claim 1, wherein the system is connected to the Internet such that a provider of the system can interact with the system.

33. The system of claim 1, wherein to configure the feature based upon the user-specific information includes deactivating the feature such that a difficulty of play is appropriate for the user.

34. The system of claim 1, wherein to configure the feature based upon the user-specific information advantageously effects a difficulty of play of the game for the user.

35. The system of claim 1, wherein to configure the feature based upon the user-specific information disadvantageously effects a difficulty of play of the game for the user.

36. The system of claim 1, wherein the user-specific information was selected about the user before the user interacted with the system.

37. The system of claim 1, wherein the user-specific information was selected by an operator of the system before the user interacted with the system for a first instance.

38. The system of claim 1, wherein the user-specific information is a characterization of the user.

39. The system of claim 1, wherein the user-specific information is how the user meets pre-selected criteria determined by a provider of the system.

40. The system of claim 1, wherein the user-specific information includes a biological profile of the user.

41. An interactive amusement system, the system comprising:
- a reader configured for reading a user-identifier associated with a user and associated with user-specific information of the user, wherein the user-specific information existed prior to the user's interaction with the system;
- a dispensing device operable to dispense an item; and
- a processor in communication with the dispensing device and the reader, the processor operable to execute coded instructions to interpret the user-identifier and configure the dispensing device in response to the associated user-specific information such that a dispensing motion of the item from the dispensing device is configured specifically for the user wherein the user-specific information is one of the user's name, address, age, gender, personal characteristic of the user, physical status of the user, legal authorization, role of the user within a group or team wherein the group or team existed prior to the user's interaction with the system, a position played or preferred prior to the user's interaction with the system for a sport, and a combination thereof.

42. The system of claim 41, wherein to configure the dispensing motion includes how the item is dispensed.

43. The system of claim 41, wherein the item is a baseball.

44. The system of claim 41, wherein the item is a tennis ball.

45. The system of claim 41, wherein the item is a soccer ball.

46. The system of claim 41, wherein to configure the dispensing device based upon the user-specific information includes activating the dispensing device such that a difficulty of play is appropriate for the user.

47. The system of claim 46, wherein appropriate for the user includes how the item is dispensed.

48. The system of claim 41 where the item is a ball; and such that a dispensing motion of the ball from the dispensing device is configured specifically for the user.

* * * * *

UNITED STATES PATENT AND TRADEMARK OFFICE
CERTIFICATE OF CORRECTION

PATENT NO. : 9,443,369 B2
APPLICATION NO. : 11/280157
DATED : September 13, 2016
INVENTOR(S) : Arthur J. Zito, Jr.

Page 1 of 1

It is certified that error appears in the above-identified patent and that said Letters Patent is hereby corrected as shown below:

In the Claims

Column 13, Line 49, delete "1" and insert --3--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*